United States Patent [19]

Kern et al.

[11] Patent Number: 5,256,156
[45] Date of Patent: Oct. 26, 1993

[54] PHYSICIAN CLOSED-LOOP NEUROMUSCULAR BLOCKING AGENT SYSTEM

[75] Inventors: Steven E. Kern, Somerville; James G. Skakoon, Melrose, both of Mass.; Dwayne R. Westenskow, Salt Lake City, Utah

[73] Assignee: Baxter International Inc., Deerfield, Ill.

[21] Appl. No.: 821,168

[22] Filed: Jan. 13, 1992

Related U.S. Application Data

[63] Continuation-in-part of Ser. No. 648,600, Jan. 31, 1991, abandoned.

[51] Int. Cl.$^5$ ................................................. A61M 5/00
[52] U.S. Cl. ............................. 604/246; 128/DIG. 13
[58] Field of Search ............... 128/DIG. 12, DIG. 13; 604/246, 67, 141, 27, 28, 31, 50, 52, 65

[56] References Cited

U.S. PATENT DOCUMENTS

| | | | |
|---|---|---|---|
| 4,308,866 | 1/1982 | Jelliffe et al. | 604/67 |
| 4,998,914 | 3/1991 | Wirst et al. | 128/DIG. 13 |
| 5,088,981 | 2/1992 | Howson et al. | 604/67 |
| 5,104,374 | 4/1992 | Bishko et al. | 128/DIG. 13 |
| 5,171,212 | 12/1992 | Buck et al. | 604/67 |

Primary Examiner—C. Fred Rosenbaum
Assistant Examiner—Manuel Mendez
Attorney, Agent, or Firm—Kane, Dalsimer, Sullivan, Kurucz, Levy, Eisele & Richard

[57] ABSTRACT

A semi-automatic infusion system for administration of neuromuscular agents and the like includes a microcomputer-controlled infusion pump with a data input pad. A clinician enters the desired paralysis level and performs periodically an electro-stimulation test to determine the actual paralysis level of the patient. This information is also entered in to the system by the physician which then calculates and administers a new dosage.

15 Claims, 3 Drawing Sheets

PHYSICIAN CLOSED-LOOP NEUROMUSCULAR BLOCKING AGENT SYSTEM

RELATED APPLICATIONS

This application is a continuation-in-part application to application Ser. No. 648,600 filed Jan. 31, 1991, now abandoned, entitled an automated infusion pump with replacement memory cartridges.

BACKGROUND OF THE INVENTION

A. Field of Invention

This invention pertains to a system for delivering neuromuscular blocking agents (NMBA) with an infusion pump. The system uses a model of the NMBA's pharmacokinetics and pharmacodynamics and quantatitive input from a clinician to adjust the infusion delivery rate of the NMBA in order to control the level of muscle paralysis while the infusion is in progress.

B. Description of the Prior Art

Neuromuscular blocking agents are routinely given during a surgical procedure by an anesthesia clinician for the purpose of providing near complete muscle paralysis during surgery. The anesthesia clinician typically creates total muscle paralysis at the start of a surgical procedure while the patient is being intubated and the initial incision is made. During the remainder of the surgical procedure, preferably the patient is under a profound but not total level of muscle paralysis to blunt any involuntary movement. By maintaining a near paralysis state with the NMBA, the clinician can easily reverse the paralysis with pharmacologic agents at any time during the procedure. If the patient is in a state of total paralysis, the clinician's ability to reverse the NMBA's effects are delayed and highly unpredictable.

To accomplish this clinical paralysis goal, the anesthesia clinician typically gives a large loading dose of the NMBA at the start of the procedure to achieve total paralysis. As this initial dose begins to wear off, the clinician then supplements the initial dose with either intermittent small bolus doses or with a continuous infusion. The level of muscle paralysis of the patient is monitored regularly using a nerve stimulator. The nerve stimulator activates a muscle and the clinician monitors manually or with instrumentation, the response to the stimulation in order to assess the degree of paralysis obtained. One method of monitoring the degree of paralysis is with a technique referred to as train-of-four (TOF). In this technique, the muscle is first stimulated with four rapid pulses. The degree of paralysis is then determined by counting the number of times the muscle twitches and the relative intensity if the twitch strength with respect to a standardized reference level. The clinical goal is to produce a relatively constant level of muscle paralysis during the procedure. Since the level of paralysis can be assessed by the clinician during the course of the procedure, feedback is available to give a indication of how well this goal is being met.

Previous studies have shown that with the newer, fast acting short duration muscle relaxants that are commonly used today, clinicians can maintain a desired constant level of paralysis better with continuous infusion than with intermittent small bolus injections. Though both techniques exhibited deviations from the desired paralysis level, the infusion group attained the desired level more often and required less manipulation by the clinician. Because the desired clinical effect, that is, muscle paralysis can be quantatitively measured with instrumentation, a complete automated NMBA delivery system was suggested whereby the clinician would specify the desired level of muscle paralysis and the infusion pump, through direct feedback of the level of paralysis, would modulate the infusion delivery rate until the desired level of paralysis was obtained. This approach has the advantage of allowing the clinician to merely specify a set point for the therapeutic goal while the device takes over control for achieving and maintaining the goal. The system produced accurate and consistent levels of muscle paralysis but was too cumbersome and expensive to be clinically useful. Moreover, it may not be desirable for the clinician to be left with the task of merely monitoring the automated delivery system.

OBJECTIVES AND SUMMARY OF THE INVENTION

In view of the above-mentioned disadvantages of the prior art, it is an objective of the present invention to provide an infusion pump system which is relatively small and inexpensive.

A further objective is to provide a system which is easy to use and which requires an input from a clinician thereby assuring his attention during a surgical procedure.

Current infusion devices require the clinician to specify drug delivery rate based on some knowledge that a specific rate for a specific patient during a specific point in the procedure is necessary to obtain the desired therapeutic goal. One advantage of the closed loop system described is that it allows the physician to specify the drug delivery in terms of the actual effect to be obtained. The disclosed invention preserves this advantage to a clinically relevant degree but does so without the additional monitoring and feedback equipment required for the closed-loop system. The disclosed invention consists of a semi-automated infusion pump that incorporates a mathematical model of the NMBA's pharmacokinetics and pharmacodynamics to determine the pump infusion rate. In addition, the user interface is organized in a manner such that the clinician inputs the desired clinical effect and the pump calculates the initial drug delivery profile based on this input and the aforementioned mathematical model.

The clinician test the effects of this initial dosage and if necessary repeats the initial phase until the patient reaches a preselected level of paralysis. Thereafter, the pump automatically delivers NMBA either in a continuous manner or in small boluses. At specific time intervals, for example after every 15 minutes, the clinician tests the paralysis level of the patient to determine whether the actual level is within a prescribed range of the preselected level. The clinician then feeds this information to the semi-automated pump. The pump uses this information to determine whether the NMBA administration should be increased, decreased, or continued unchanged. At the end of the surgical procedure, the clinician activates the pump controls to terminate the infusion.

DETAILED DESCRIPTION OF THE INVENTION

Figure 1:
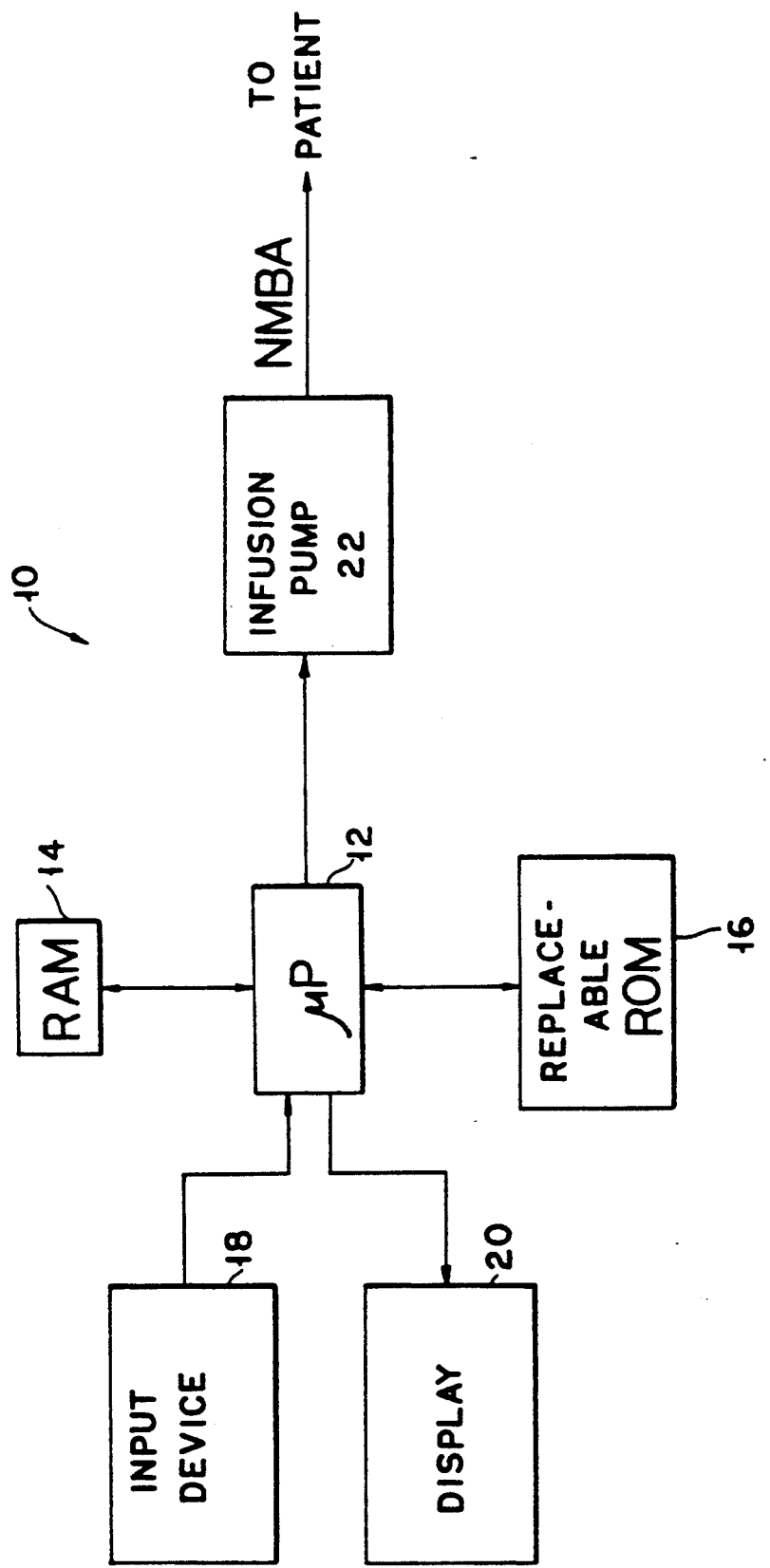
FIG. 1 shows a block diagram for a system constructed in accordance with this system.

Referring now to the drawings, as shown in FIG. 1, a system 10 constructed in accordance with this invention consists of a microprocessor 10 coupled in the usual manner to RAM 14, a ROM 16, an input device 18, and a display device 20. The microprocessor 12 is used to control the operation of an infusion pump 22 used to administer NMBA to a patient. The system 10 may be similar to the automated infusion pump disclosed in co-pending application Ser. No. 648,600 mentioned above, with the microprocessor 12 and its related components being mounted in or on the housing of pump 22. The input device 18 may be a keyboard, and the display device may be, for example, a liquid crystal display. ROM 16 is used to provide the control program for the microprocessor. Preferably, ROM 16 is an electrically erasable read-only memory housed in a replaceable cartridge which may be changed at will to match different NMBA, different means of testing the paralysis level of a patient, and so on. RAM 14 is used by the microprocessor for temporary data storage in the usual manner.

Figure 2:
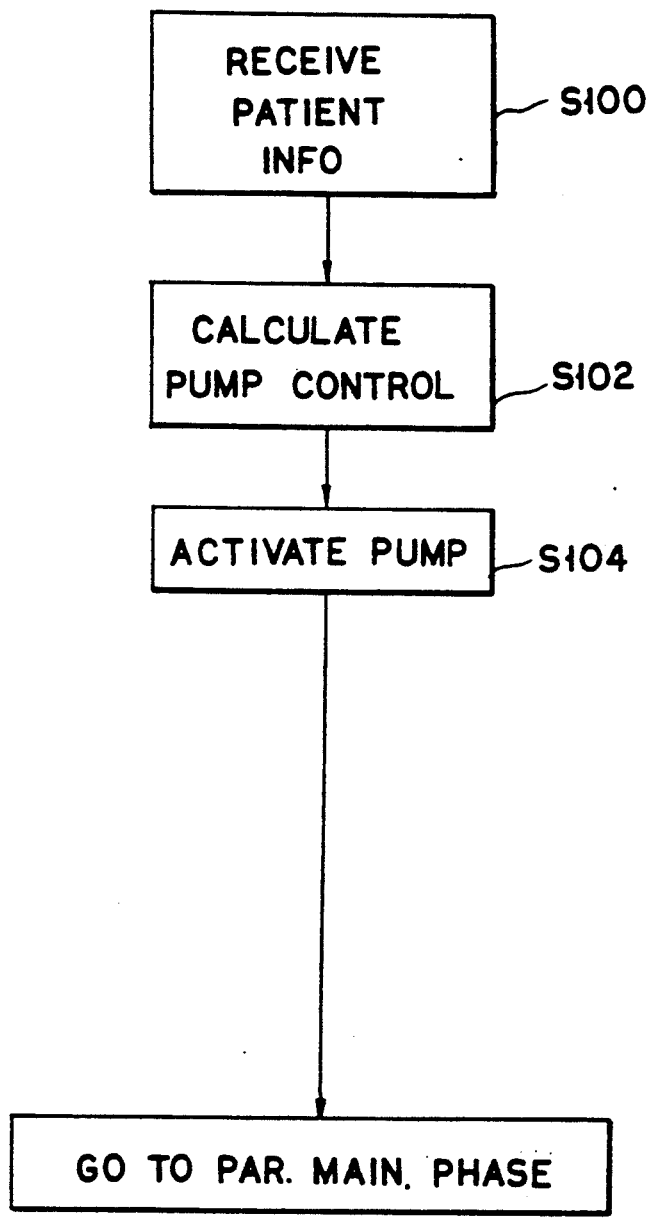
FIG. 2 shows a flow chart for the system of FIG. 1 during the initiation phase; an FIG. 3 shows a flow chart for the system of FIG. 1 during the paralysis maintenance phase.

Referring now to FIG. 2, for the initial phase of the procedure, the clinician provides information on the patient in step 100. The clinician will specify a loading dose based for example, on the ED95 dose for the drug. The ED95 dose refers to the dose effective for achieving a desired outcome in 95% of the patient population. For example, the clinician may specify a dose that is 2-3 times the ED95 dose. In this stage the clinician may also specify the level of paralysis that is to be attained in the course of surgery. In step S102 the pump control signal is calculated for the pump to deliver the required dose. In step S104, the pump is activated to deliver the initial dose, thereby completing the initial phase.

Figure 3:
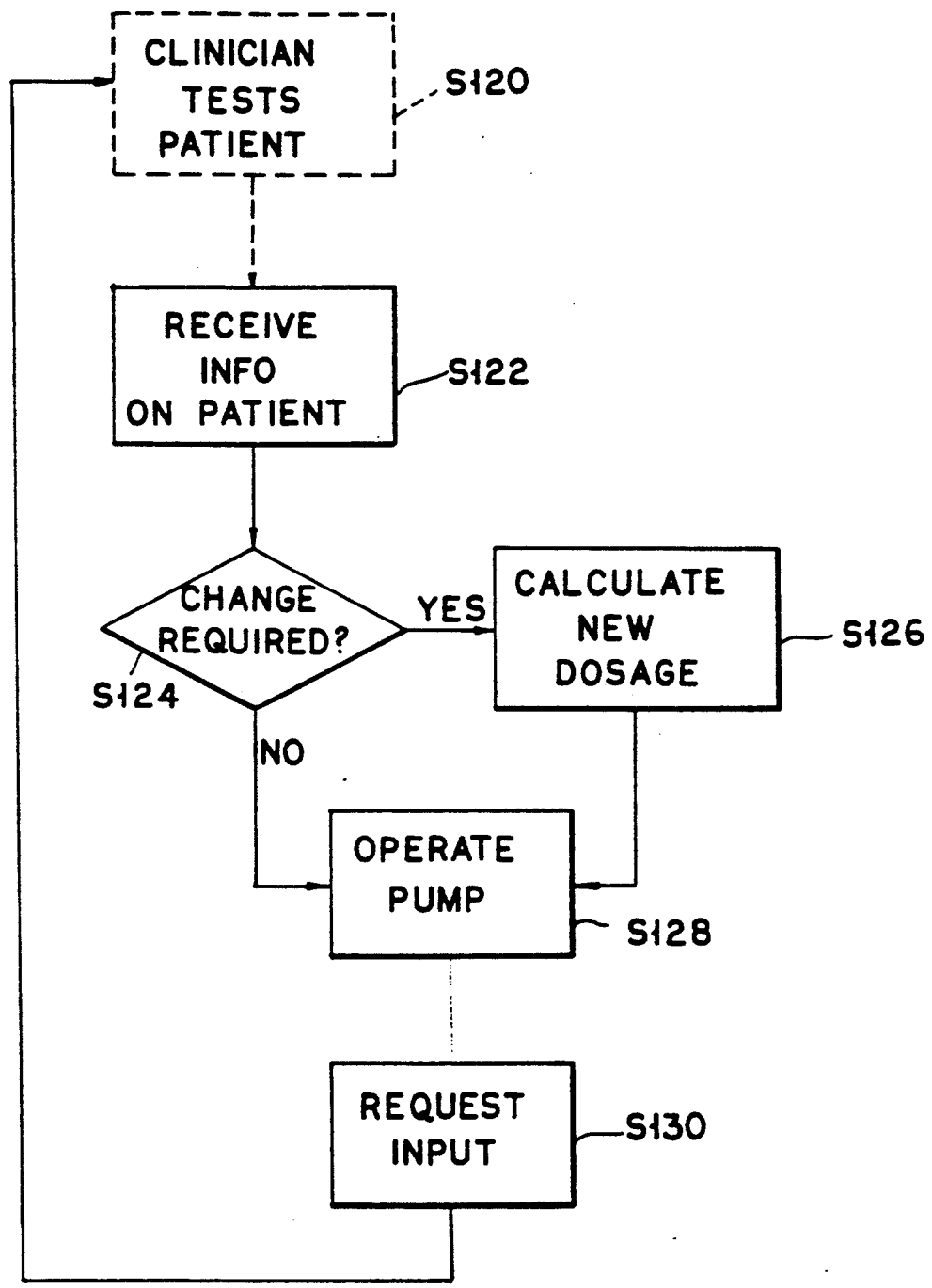

Initially, as discussed above the patient is subjected to complete paralysis. As the effects of the initial dose wear off, the system switches over to the maintenance phase illustrated in FIG. 3. In this phase, in step 120, the clinician tests the patient for paralysis level and feeds the result of the test to the system in step S122. In step 124, the system (i.e. the microprocessor) compares the result obtained by the physician to the desired paralysis level that was initially set, and determines whether the dosage of NMBA is adequate. If it is found the dosage is too high or too low, in step S126, the new dosage is calculated. In step S128, the pump is operated to deliver either the old dosage or the new dosage calculated in step S126. In case of a continuous infusion mode, in step S128, the rate of infusion is either maintained constant, increased or decreased. In step S130, after a determined time period, the 10 systems requests that the physician test the patient again (for example via display 20), and the system returns to step S120.

As previously mentioned, the precise level of paralysis can be measured by different methods. One such method consists of counting the number of muscle twitches elicited from repeated stimulation. The subject system may use the number of twitches in response to the stimulation as its feedback input in step S122. The number of response twitches has been clinically shown to be an approximate indication of paralysis level. This information gives a good enough relative criteria to be used as a feedback signal to the pump for modulation of the infusion rate to maintain a steady level of relaxation. The TOF count is easily obtained by stimulating a muscle, usually the adductor pollices muscle of the hand, and counting how many times the patient's thumb flexes in response to the stimulation. This TOF count is then entered into the semi-automatic pump. If the number is different from the desired number set by the clinician, the pump changes the drug delivery profile based on the mathematical model and the difference in the desired TOF count and actual TOF count as described above.

While the TOF count is a standard-measure used to clinically assess the level of paralysis, other clinically useful methods will also be accommodated by the device. The user, for example, may select the method used for assessing levels of paralysis by inserting into the pump the appropriate ROM cartridge. The ROM includes the appropriate mathematical model that represents the method. Other means of determining the paralysis level include post-tetanic twitch count, double-burst stimulation and direct percent relaxation indicated by a relaxation monitoring device.

The disclosed invention offers the following distinguishing advantages:

A. The clinician inputs the desired therapeutic effect (i.e. the TOF count) and the pump automatically determines the infusion profile necessary to achieve the desired effect. The clinician no longer needs to memorize drug dose amounts but instead works directly to specify the desired effect.

B. The pump allows for feedback by the physician with an easily obtained quantitative value for correction of the delivery profile to meet the desired therapeutic effect.

C. The physician provides the feedback instead of requiring extra monitoring equipment for modulating the delivery profile.

Obviously, numerous modifications can be made to this invention without departing from its scope as defined in the appended claims.

We claim:

1. An apparatus for administering a neuromuscular blocking agent to a patient to induce paralysis, said apparatus comprising:

means for pumping a neuromuscular blocking agent to a patient;

means for controlling the operation of said means for pumping, including manual controls for manually setting the preliminary desired operation of said pumping means and further including means for entering the desired results of patient electro-stimulation test; and means for periodically entering the actual results of patient electro-stimulation tests;

wherein said means for controlling alters the operation of said pumping means when said actual results differ from said desired results.

2. The apparatus of claim 1 wherein said electro-stimulation test is a train-of-four test.

3. The apparatus of claim 1 further comprising replaceable memory means, said replaceable memory means being tailored to match a preselected electro-stimulation test, preselected therapeutic agent, preselected therapeutic time course, or combination thereof.

4. The apparatus of claim 1 wherein said means for pumping comprises an infusion pump.

5. An apparatus for administering a neuromuscular blocking agent into a patient to induce a selectable level of paralysis, said apparatus comprising:

infusion pump means for infusing said agent to said patient;

microprocessor means coupled to said infusion pump means for controlling the operation thereof;

data input means coupled to said microprocessor means for entering a first signal indicative of a desired paralysis level and a second signal indicative of the actual paralysis level of said patient based on a preselected test; and memory means for storing a program for said microprocessor corresponding to said agent and said test, responsive to which program, said microprocessor determines the operation of said infusion pump.

6. The apparatus of claim 5 wherein said infusion pump operates in a continuous mode.

7. The apparatus of claim 5 wherein said infusion pump delivers said agent in a bolus mode.

8. The apparatus of claim 5 wherein said memory means comprises a replaceable ROM.

9. The apparatus of claim 5 wherein said second signal corresponds to the results of a train-of-four test.

10. The apparatus of claim 5 further comprising display means for displaying instructions.

11. A method of administering a neuromuscular blocking agent for inducing a preselectable level of paralysis on a patient comprising the steps of:

providing an infusion pump system for infusing said patient;

microprocessor means coupled to said infusion pump system for controlling the operation thereof;

data input means coupled to said microprocessor;

entering in said data input means a predetermined level of paralysis;

monitoring said patient to determine his actual level of paralysis;

entering said actual level in said data input means; and adjusting the infusion of said agent to said patient in accordance with the difference between said actual and predetermined level of paralysis.

12. The method of claim 11 wherein said actual paralysis level is determined by conducting a electro-stimulation test.

13. The method of claim 12 wherein said test is a train-of-four test.

14. The method of claim 11 wherein said infusion pump system includes a replaceable memory unit, and further comprising the step of installing a memory unit corresponding to a preselected agent and test.

15. The method of claim 11 further comprising the step of administering an initial dose of said agent to establish paralysis in said patient by administering a multiple of the ED95 dose.

* * * * *

UNITED STATES PATENT AND TRADEMARK OFFICE
CERTIFICATE OF CORRECTION

PATENT NO. : 5,256,156
DATED : October 26, 1993
INVENTOR(S) : Steven E. Kern, James G. Skakoon, Dwayne R. Westenskow It is certified that error appears in the above-identified patent and that said Letters Patent is hereby corrected as shown below:

Column 1, line 58, "a" should be --an--.
Column 2, line 68, "an" should be --and--.
Column 3, line 56, delete "10".
Column 6, line 15, "a" should be --an--.

Signed and Sealed this

Tenth Day of May, 1994

Attest:

BRUCE LEHMAN

Attesting Officer    Commissioner of Patents and Trademarks